United States Patent [19]

Randen

[11] Patent Number: 4,940,579

[45] Date of Patent: Jul. 10, 1990

[54] TOPICAL APPLICATION OF MEDICAMENT IN A BINDER

[75] Inventor: Neil A. Randen, Stillwater, Minn.

[73] Assignee: Minnesota Mining and Manufacturing Company, St. Paul, Minn.

[21] Appl. No.: 290,579

[22] Filed: Dec. 27, 1988

[51] Int. Cl.$^5$ ............... A61K 31/74; A61K 31/78; A61K 13/02; A61K 9/10

[52] U.S. Cl. .................................. 424/78; 424/81; 424/448; 424/447; 424/449; 514/937

[58] Field of Search ............... 424/28, 81, 448, 447, 424/449; 514/937

[56] References Cited

U.S. PATENT DOCUMENTS

| | | | |
|---|---|---|---|
| 3,896,789 | 7/1985 | Trancik | 128/2 |
| 3,928,261 | 12/1975 | Scherther | 424/78 |
| 4,008,321 | 2/1977 | Kamishita et al. | 424/243 |
| 4,172,122 | 10/1979 | Kubik et al. | 424/59 |
| 4,181,786 | 1/1980 | Mune et al. | 525/327 |
| 4,248,855 | 2/1981 | Blank et al. | 424/19 |
| 4,250,163 | 2/1981 | Nagai et al. | 424/14 |
| 4,310,509 | 1/1982 | Berglund et al. | 424/81 |
| 4,316,887 | 2/1982 | Kamishita et al. | 424/81 |
| 4,374,126 | 2/1983 | Cardarelli et al. | 424/81 |
| 4,552,755 | 11/1985 | Randen | 424/81 |
| 4,761,288 | 8/1988 | Merei | 514/78 |
| 4,816,256 | 3/1989 | Randen | 424/487 |

FOREIGN PATENT DOCUMENTS

| | | | |
|---|---|---|---|
| 0188793 | 2/1977 | European Pat. Off. | |
| 0055857 | 7/1982 | European Pat. Off. | |
| 1465665 | 2/1977 | United Kingdom | |
| 1548837 | 7/1979 | United Kingdom | 514/937 |
| 1593097 | 7/1981 | United Kingdom | |
| 2096890 | 10/1982 | United Kingdom | |

*Primary Examiner*—Joseph L. Schofer
*Assistant Examiner*—Carmen B. Pili-Curtis
*Attorney, Agent, or Firm*—Donald M. Sell; Walter N. Kirn; Mark A. Litman

[57] ABSTRACT

The application of medicaments to non-mucosal areas of mammal bodies is enhanced by the use of a polymeric composition. The mixture of medicament and pressure-sensitive polymeric adhesive in specified proportions forms a non-self-supporting film coating on the mammal which provides a good medicinal application.

25 Claims, No Drawings

TOPICAL APPLICATION OF MEDICAMENT IN A BINDER

BACKGROUND OF THE INVENTION

1. Field of the Invention

Medicaments (with a substantive polymeric binder) are applied to mammalian bodies. The binder is present in insufficient quantities (proportion to the medicament) to form a continuous of porous film).

2. Background of the Art

Substances with medicinal value are often to be applied to the exterior of mammalian bodies, including those of humans. Materials such as antibiotics, fungicides, antiseptics, anaesthetics, antipruretics, antiinflammatants, and the like are commonly applied to the skin for their medicinal effects. Some are added as powders (e.g., antifungal materials), creams or ointments (e.g., antibiotics, antiinflammatants, antifungal materials, antipruretics, etc.), and as solutions (e.g., anaesthetics, styptics, etc.). These materials have variable persistance and stability when applied in this manner. Powders and dispersions tend to rub off, materials applied from solution tend to wash off easily with perspiration, and creams and ointments tend to be messy and rub off easily.

In order to overcome some of these problems with topical applications of medicaments, polymers are sometimes used to bind the medicaments in a membrane or film on the skin or hair. The medicament then migrates out of the polymer and medicinal activity is maintained at the interface of film and skin. Medicament will also pass into the skin or blood stream from these films.

U.K. Patent No. 2,096,890 describes the use of an antiinflammatory analgesic cataplasm containing indomethacin as the medicinally active ingredient. Pastes are applied to the skin in a cloth and polymeric films are placed over the cloths.

U.K. Patent No. 1,593,097 discloses the application of a gell composition containing medicine to the skin. Thickening agents, including polymeric thickening agents, are used to form the gel along with the medically active ingredient and a mixture of solvents.

U.K. Patent No. 1,465,665 shows the use of a polymeric binder in a solution for the topical application of medicinal ingredients such as antiinflammatants, analgesics, and antipruritics. It is stated that by using a small quantity of carboxyvinyl polymer, excellent topical compositions are formed which are not tacky when applied to the skin and quickly form membranes.

U.S. Pat. No. 4,250,163 discloses a method and composition for the application of medicament to the mucosa of the oral or nasal cavity. A polymeric binder comprising a water-swellable and mucosa-adhesive composition comprising a matrix of cellulose ether and an acrylic polymer.

U.S. Pat. No. 4,008,321 discloses the use of a carboxyvinyl polymer in an aqueous medium to form medicinal compositions for topical applications. A transparent gelatinous topical composition is formed.

U.S. Pat. No. 4,248,855 discloses a method and composition for dispensing salt-forming pharmaceutically effective compounds orally, topically, or systemically. A salt of a polymer containing acid groups is combined with the effective compounds to form solutions, suspensions, emulsions or shaped body (e.g., eye insert).

U.S. Pat. No. 4,374,126 discloses a film forming antimicrobial material comprising an alcohol soluble carboxylated polyacrylate containing an antimicrobial agent and adhesion promoter.

U.S. Pat. No. 3,896,789 discloses a tape containing retinoic acid in a continuous pressure sensitive adhesive layer on one side of the tape. The tape is adhered to the body for topical treatment with retinoic acid.

U.K. Pat. No. 1,548,837 discloses the topical application to skin of films containing medicaments. The films are flexible, continuous, and non-tacky and provide enhanced delivery through dermal layers U.S. Pat. No. 4,310,509 describes a pressure sensitive adhesive having an antimicrobial agent therein An adhesive matrix is formed and then spread or coated onto backing materials. For example, a dried film of the adhesive is laminated to polyethylene film (Example 1).

U.S. Pat. No. 4,181,786 discloses antibacterial and antifungal metal ions bonded to a carboxyl group containing polymer for topical application. The material is generally to be provided as a shaped article such as a film (column 5, lines 54–66).

U.S. Pat. No. 4,316,887 discloses a medicinal composition for topical applications comprising the medically active ingredient in a water soluble carboxyvinyl copolymer.

U.S. Pat. No. 4,552,755 describes an improved oil-in-water moisturizing composition comprising an oil phase containing an emollient oil and an oil-soluble acrylate polymer, a water phase and an emulsifying agent. The polymer improves the substantivity of the composition. These polymers are generally useful in the practice of the present invention.

U.S. Pat. No. 4,172,122 describes the topical application of sunscreen materials in a substantive composition. The composition comprises an oil base, UV light absorbing material, and at least 0.5 percent by weight of a water-insoluble acrylate polymer. These polymers are useful in the practice of the present invention.

EPO Application No. 0 188 793 A1 discloses the use of hydroxy (lower alkyl) acrylate or methacrylate polymers to improve the performance of hydroalcoholic solutions of minoxidil for topical use. The polymers are hydrophilic since they are to be used with hydroalcoholic (water/alcohol) solutions.

SUMMARY OF THE INVENTION

Medicaments are topically applied in a non-film forming liquid medium containing from 0.25 to 10% by weight of pressure-sensitive adhesive polymer and 0.1 to 50% by weight of medically active ingredients. The composition when applied and dried of carrier liquid or solvent forms a coating which has no significant cohesive strength (does not form a self-sustaining or strippable film) and is non-tacky to the touch. The medicament has affinity for the adhesive polymer and is effectively held against or transferred to the skin from the adhesive polymer

DETAILED DESCRIPTION OF THE INVENTION

The topical application of medicaments to the skin has traditionally been done with the application of self-sustaining cohesive articles such as films, tapes, or plasters as a proposed improvement over direct applications of powders, ointments, creams, lotions or the like. It has been felt that these more substantial media provided a longer lasting and more controllable application of medicine to the skin or hair of a mammal. These medical applications suffer from distinct problems of their own, however. All of the films and tapes tend to be uncomfortable as they cannot completely conform with stretching, bending, or wrinkling which the exterior surfaces of bodies undergo during movement. The films, tapes and plasters are not cosmetically acceptable, especially if applied to the face and hands which are exposed to view. Films and tapes are easily and accidentally removed, in part or in whole, from the skin by inadvertent contact or perspiration occurring under the film or tape. This directly reduces the medical efficiency of the application Films and tapes can trap moisture against the surface which can be medically disadvantageous and can block oxygen penetration to the surface. The application of thin polymer films will not solve these problems because the films can be readily broken and delivery of the medicine can be interrupted.

It has been found in the present invention that by selecting only appropriate proportions of medicaments and pressure-sensitive adhesive polymeric binders in solutions, emulsions, or dispersions that an extremely effective topical application of medicaments may be performed. The proportions are selected, contrary to conventional wisdom, so that a non-cohesive, non-tacky coating of the binder and medicament is formed on the skin or hair in non-mucosal areas.

Medicaments according to the practice of the present invention are those compounds or materials which have a direct medicinal or neurological effect (excluding alcohols). Materials which have a beneficial activity against the growth, propogation or survival of bacteria, fungi, or viruses or which are antihistamines, antitoxins, anaesthetics, analgesics, antipruritics, vitamins, and antiinflammatants are included in the term medicaments. These materials are well known in the medical art and no exhaustive list is thought to be necessary. Exemplary compounds include hydrocortisone acetate, undecylenic acid, tolnaftate, methyl salicylate, lidocaine, oxytetracycline.HCl, retinoic acid, Minoxidil® (6-Amino-1,2-dihydro-1-hydroxy-2-imino--piperidinopyrimidine), etc. These medicaments may provide the medicinal activity at the site of application or upon absorption through the skin.

These medicaments are combined in the critical proportions of this invention with oil compatible pressure sensitive adhesives. Pressure-sensitive adhesives are art recognized as a standard class of materials. These are adhesives which in dry (substantially solvent free except for residual solvent) form are aggressively and permanently tacky at room temperature (e.g., 15 to 25° C.) and firmly adhere to a variety of dissimilar surfaces upon mere contact without the need for more than manual pressure. They require no activation by water, solvent or heat in order to exert a strong adhesive holding force towards such materials as paper, cellophane, glass, wood and metals. They have a sufficientyl cohesive holding and elastic nature so that, despite their aggressive tackiness, they can be handled with the fingers and removed from smooth surfaces without leaving a substantial residue (cf. Test Method for Pressure-Sensitive Tapes, 6th Ed., Pressure Sensitive Tape Council, 1953). Pressure-sensitive adhesives and tapes are well known, and the wide range and balance of properties desired in such adhesives has been well analyzed (cf. U.S. Pat. No. 4,374,883; and "Pressure-Sensitive Adhesives" in *Treatise on Adhesion and Adhesives* Vol. 2, "Materials", R. I. Patrick, Ed., Marcel Dekker, Inc., N.Y., 1969). The various materials and compositions useful as pressure-sensitive adhesives are available commercially and are thoroughly discussed in the literature (e.g., Houwink and Salomon, *Adhesion and Adhesives*, Elsevier Publ. Co., Amsterdam, Netherlands, 1967; Handbook of Pressure-Sensitive Adhesive Technology, Donates Satas, Ed., VanNostrand Reinhold Co., N.Y., 1982).

Pressure-sensitive adhesives are generally chemically composed of rubber-resin materials, acrylic resins, polyurethane resins, silicone resins, and the like. Among the various patent literature describing compositions and improvements in pressure-sensitive adhesive formulations are U.S. Reissue Pat. No. 24,906; U.S. Pat. No. 2,652,351; U.S. Pat. No. 3,740,366; U.S. Pat. No. 3,299,010; U.S. Pat. No. 3,770,708; U.S. Pat. No. 3,701,758; U.S. Pat. No. 3,922,464; U.S. Pat. No. 3,931,087; U.S. Pat. No. 4,012,560; U.S. Pat. No. 4,077,926; U.S. Pat. No. 4,387,172; U.S. Pat. No. 4,418,120; U.S. Pat. No. 4,629,663; and the like. These classes of rubber resin, acrylic, silicone and polyurethane pressure-sensitive adhesives as well as any other pressure-sensitive adhesives are generally useful in the present invention. Surprisingly, when pressure sensitive adhesives are used in the detailed proportions of the present invention, non-tacky applications of medicaments are provided. The preferred adhesives are the acrylate polymers (homopolymers, copolymers, terpolymers, etc.) described in U.S. Pat. No. 4,172,122 and variations thereof. The polymers useful in the present invention are oil compatible and generally are clearly hydrophobic in their properties.

Acrylate polymers used as binders for the medicaments include homopolymers, copolymers, terpolymers, etc., derived from the same or different ester monomers of the formula:

Formula I where $R^1$ is alkyl containing 1 to 18 carbon atoms in straight or branched-chain configuration, $R^2$ is hydrogen, methyl or $-CH_2CO_2H$, and $R^3$ is hydrogen, $-CO_2H$ or $CO_2R^1$, provided that $R^3$ or $R^2$ or both are hydrogen. The polymer may optionally contain up to 40 mole percent of the same or different acid monomers of the formula:

Formula II where $R^4$ is hydrogen or $-CO_2H$, and $R^5$ is hydrogen, methyl, or $-CH_2COH$, provided that $R^4$ or $R^5$ or both are hydrogen.

The acrylate polymers can be prepared from the corresponding alkyl esters of acrylic, methacrylic, itaconic or maleic acid, wherein the ester alkyl groups may contain 1 to 18 carbon atoms and are exemplified by methyl, ethyl, butyl, methylisoamyl, n-hexyl, 2-ethylhexyl, isooctyl, isodecyl, lauryl, octadecyl, stearyl groups and the like. The most preferred esters are the acrylates and methacrylates with alkyl groups containing 6 to 18 carbon atoms. Esters wherein the alkyl group contains less than four carbon atoms may be included in small amounts, e.g. less than 10 mole percent. However, in order to achieve the requisite solubility parameter, the polymers should generally not contain a significant amount of lower alkyl ester monomers.

The acrylate polymers may optionally contain up to 40 mole percent of the unesterified $\alpha,\beta$-olefinically unsaturated carboxylic acids of Formula II such as acrylic acid, methacrylic acid or up to 20 mole percent of the difunctional acids—maleic acid or itaconic acid. The presence of the carboxylic acid monomer enhances the removability of the compositions with soap and water. Polymers containing carboxylic acid groups are also useful as emulsifiers and should be used in the water-in-oil emulsion formulations.

The preferred polymers for the oil and oil in water emulsion compositions (as distinguished from the water-in-oil emulsions) are derived from 0 to 30 mole percent of the acid monomers and from 100 to 70 mole percent of the alkyl ester monomers. The more preferred polymers are derived from 5 to 25 percent of the acid monomers and from 95 to 75 mole percent of the alkyl ester monomers with the alkyl groups in the latter containing from 6 to 18 carbon atoms. The most preferred polymers for the oil compositions are derived from 5–15 mole percent of the acid monomers and from 95 to 85 mole percent of alkyl ester monomers having 6 to 18 carbon atoms in the ester alkyl group.

The preferred polymers for the water-in-oil emulsion compositions are derived from 5 to 40 mole percent of the acid monomers and 95 to 60 mole percent of the alkyl ester monomers. The more preferred polymers are derived from 10 to 30 mole percent of the olefinically unsaturated carboxylic acid monomers and 90 to 70 mole percent of the alkyl ester monomers containing 6 to 18 carbon atoms in the ester alkyl groups. The most preferred polymers are derived from 15 to 30 mole percent of the acid monomers and 85 to 70 mole percent of the alkyl ester monomers containing 6 to 18 carbon atoms in the ester alkyl groups.

The preparation of the polymers from the olefinically unsaturated monomers is well documented in the literature and can be carried out by standard bulk, solution or emulsion techniques. Generally, the latter two are preferred with solution polymerization being most preferred. The polymerization of the monomers is catalyzed by free radical-generating catalysts such as peroxides, azo catalysts and the like. To be most effective, the reactor for such polymerizations should be purged with an inert gas in order to remove traces of oxygen. The solution polymerizations are run in a compatible solvent and the final polymer solution preferably contains 30 to 60 percent solids.

The molecular weight of the polymers used in the compositions may vary over a broad range. The molecular weight must be suitably large to provide the requisite binding effect. The upper limit is determined only by formulation requirements. As the molecular weight increases, the polymers tend to become too viscous to formulate easily into cosmetically-appealing compositions. Generally, polymers having a Brookfield viscosity between 50 and 100,000 cps and preferably between 500 and 15,000 cps, when measured at 16.6 percent non-volatiles will be useful in the compositions of the invention.

The acrylate polymers useful in the compositions are insoluble in water and must have a solubility parameter between about 6 and 10 in poorly and moderately hydrogen bonding solvents. The method for determining solubility parameter ranges of polymers and an extensive list of solvents (classified as either poorly hydrogen bonding, moderately hydrogen bonding, or strongly hydrogen bonding) are described in *Polymer Handbook* (edited by Bandrup and Immergut), pages IV-344–358. Acrylate polymers having the requisite solubility parameter will be soluble in the oil base of the compositions.

The compositions of the invention are of three basic types, i.e., oils, water-in-oil and oil-in-water emulsions. The oil formulations are prepared by mixing the oil base, polymer and medicament together and warming the mixture with slow agitation to about 140° F. The water phase ingredients, if part of an emulsion formulation, are combined and heated to 180° F. This phase is slowly added to the oil phase ingredients, also at 180° F., and the combination allowed to cool with agitation. The formulations generally contain about 0.5 to 10 percent by weight of the acrylate polymer, with the preferred range being from about 0.5 to 5.0 percent by weight. At levels below 0.25 percent, the polymer is less effective in holding a significant amount of the medicament on the skin when the skin is exposed to water. At levels above 10 percent, the formulation generally becomes sticky and develops an unpleasant feeling.

The cosmetic oil base, if any, of the compositions may be solid or liquid, but the entire formulation should be somewhat fluid at skin temperatures for ease of application. Fragrances, fillers, dyes, colorants, preservatives, antioxidants and other such material may be included in minor amounts in the compositions without affecting the substantivity of the composition.

When applied to human skin, these products form films of the medicament on the skin surface. The polymer dispersed therein holds the medicament onto the skin so that a significantly greater pharmacological benefit is provided than the compositions without the polymer.

As indicated above, the composition to be applied to topical areas of mammals (generally non-water dwelling mammals) comprises 0.25–10% by total weight of polymer, preferably 0.5 to 7 percent by weight, and most preferably 0.5 to 2% by weight of polymer per total weight of composition. The medicament may be present in a broader weight range of 0.1 to 50% by total weight of the composition, preferably 0.25 to 20% by weight, more preferably 0.5 to 10% and most preferably 1 to 3% by weight. The ratio of the polymer to medicament (wt. polymer/wt. medicament) must also be in the range of 1/5 to 1/50 to achieve the benefits of the present invention.

These and other aspects of the invention will be shown in the following non-limiting examples.

EXAMPLES

The preferred acrylate polymers of this invention have solubility parameters of 6–10 $(cal./cc.)^{\frac{1}{2}}$ in poorly and moderately hydrogen bonding solvents. They are depicted by the following structure:

All of the actives formulated with the polymers were retained on the skin at higher retention values than their corresponding controls.

TABLE I

| | | | Percent Active Retention After a Water Assault | |
|---|---|---|---|---|
| OTC Category | Active | Polymer Mole Ratio Mono. | % Retention Control | w/Poly. |
| Antipruritic | Hydrocortisone Acetate | 4:5:91 AA:SMA:IOA | 60.6 | 70.0 |
| | | 16:25:59 AA:SMA:IOA: | 67.2 | 81.2 |
| Antifungal | Undecylenic Acid | 90:10 IOA:AA | 44.0 | 69.0 |
| | | 50:30:20 IOA:SMA:AA | 47.0 | 66.0 |
| Antifungal | Tolnaftate | 50:40:10 IOA:SMA:AA | 71.0 | 100.0 |
| | | 90:10 IOA:AA | 80.0 | 99.0 |
| External Analgesic | Methyl Salicylate | 90:10 IOA:AA | 4.0 | 17.0 |
| | | 50:40:10 IOA:SMA:AA | 2.0 | 28.0 |
| | | 50:30:20 IOA:SMA:AA | 8.0 | 24.0 |
| Anaesthetic | Lidocaine | 90:10 IOA:AA | 26.0 | 87.0 |
| | | 50:40:10 IOA:SMA:AA | 14.0 | 76.0 |
| | | 50:30:20 IOA:SMA:AA | 37.0 | 76.0 |
| Antimicrobial | Oxytetracyline.HCl | 50:30:20 IOA:SMA:AA | 61.0 | 82.0 |
| | | 50:40:10 IOA:SMA:AA | 17.0 | 47.0 |
| | | 990:10 IOA:AA | 35.0 | 76.0 |
| Antiseptic | Camphor, Phenol* | 50:30:20 IOA:SMA:AA | 26.0 | 83.0 |
| | | 50:40:10 IOA:SMA:AA | 35.0 | 100.0 |
| Antiseptic | Camphor, Phenol** | 50:40:10 IOA:SMA:AA | 8.0 | 61.0 |
| | | 50:30:20 IOA:SMA:AA | 7.0 | 59.0 | acrylic acid = AA
stearyl methacrylate = SMA
isooctyl acrylate = IOA
*water-in-oil emulsion
**oil formulation

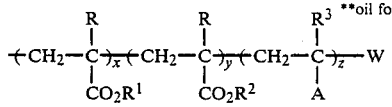

(R's on different monomers don't have to be the same)

where:
R = —H, —CH$_3$, —CH$_2$CH$_3$
R$^1$ = —CH$_3$ thru C$_{18}$ alkyl
R$^2$ = —CH$_3$ thru C$_{18}$ alkyl
R$^3$ = —H, —CH$_3$, —CH$_2$CO$_2$H
A = —CO$_2$H, C(O)B(CH$_2$)$_n$N(D)$_2$
  where
  B = —O—, —NH—
  D = —CH$_3$, —CH—CH$_3$
  n = 2, 3
W = other monomers
x + y + z = 100

A few of the topical over-the-counter drug categories where the polymers provide an increased substantivity benefit are antifungals, antipruritics, external analgesics, antiseptics, anaesthetics, antimicrobials and the like. To demonstrate the utility of the invention, the percent retentions of those actives on the skin after a water bath assault were determined. Formulations containing the actives (control) were compared to those also containing the polymer. The data are in Table I.

The following example shows the polymer composition versus the percent vitamin A palmitate retention after a water assault. It should be noted that the seemingly large statistical variation is the result of the fact that animal bodies and even bodies amongst a single species are very different.

| Polymer Mole Ratio | | | Percet Vitamin A Palmitate Retention | | |
|---|---|---|---|---|---|
| Stearyl Methacrylate | Acrylic Acid | Isooctyl Acrylate | with Polymer | Control | Difference |
| 10 | 10 | 80 | 90.8 ± 2.1 (n = 2) | 56.0 ± 7.6 | +34.8 |
| 40 | 10 | 50 | 81.3 ± 7.4 (n = 5) | 53.1 ± 11.2 | +28.2 ± 18.2 |
| 10 | 20 | 70 | 71.3 ± 14.5 (n = 3) | 61.6 ± 6.0 | +9.6 ± 8.7 |
| 40 | 20 | 40 | 85.0 ± 0 (n = 2) | 49.5 ± 2.2 | +35.5 ± 2.2 |
| 25 | 15 | 60 | 75.0 ± 10.3 (n = 5) | 54.3 ± 10.5 | +20.1 ± 2.4 |

I claim:

1. A liquid composition for topical application to the non-mucosal, non-oral, skin and/or hair of a mammal comprising a solution, emulsion or dispersion of 0.25 to 10% by weight of an oil compatible pressure-sensitive adhesive polymer, 0.1 to 50% by weight of a medicament, and 49.75 to 99.65% by weight of a carrier liquid, the ratio of said polymer to medicament being in the range of 1/5 to 1/50, said composition being incapable of forming a self-sustaining film when applied as a wet coating of 25 microns and dried.

2. The composition of claim 1 wherein said pressure sensitive adhesive comprises an acrylate.

3. The composition of claim 1 wherein said pressure sensitive adhesive comprises a silicone resin.

4. The composition of claim 1 wherein said pressure sensitive adhesive comprises a polyurethane resin.

5. The composition of claim 1 wherein said pressure sensitive adhesive is present as 0.5 to 5% by weight of said composition.

6. The composition of claim 2 wherein said pressure sensitive adhesive is present as 0.5 to 5% by weight of said composition.

7. The composition of claim 1 wherein said medicament is present as 0.25 to 20% by weight of said composition.

8. The composition of claim 2 wherein said medicament is present as 0.25 to 20% by weight of said composition.

9. The composition of claim 5 wherein said medicament is present as 0.25 to 20% by weight of said composition.

10. The composition of claim 6 wherein said medicament is present as 0.25 to 20% by weight of said composition.

11. The composition of claim 1 wherein said medicament is selected from the class consisting of materials which have an activity against the growth, propagation and/or survival of bacteria, fungi, or viruses.

12. The composition of claim 2 wherein said medicament is selected from the class consisting of materials which have an activity against the growth, propagation and/or survival of bacteria, fungi, or viruses.

13. The composition of claim 10 wherein said medicament is selected from the class consisting of materials which have an activity against the growth, propagation and/or survival of bacteria, fungi, or viruses.

14. The composition of claim 1 wherein said medicament is selected from the class consisting of antihistamines, antitoxins, anaesthetics, analgesics, antipruritics, and antiinflammatants.

15. The composition of claim 2 wherein said medicament is selected from the class consisting of antihistamines, antitoxins, anaesthetics, analgesics, antipruritics, and antiinflammatants.

16. The composition of claim 10 wherein said medicament is selected from the class consisting of antihistamines, antitoxins, anaesthetics, analgesics, antipruritics, and antiinflammatants.

17. The composition of claim 1 wherein said medicament comprises an antibiotic, bacteriastat, bactericide, or antifungal compound.

18. A method of medically treating a mammal comprising applying the composition of claim 1 to a non-mucosal area of said mammal and spreading said composition so that a non-self-sustaining coating is formed over an area.

19. The composition of claim 6 wherein said medicament comprises 6-amino-1,2-dihydro-1-hydroxy-2-imino-4-piperidinopyrimidine.

20. A liquid composition for topical application to the non-mucosal, non-oral, skin and/or hair of a mammal comprising a solution, emulsion or dispersion of 0.25 to 10% by weight of an oil compatible pressure-sensitive adhesive polymer, 0.to 50% by weight of a medicament, and 49.75 to 99.65% by weight of a carrier liquid, the ratio of said polymer to medicament being in the range of 1/5 to 1/50, said composition being non-tacky to the touch and incapable of forming a self-sustaining film when applied as a wet coating of 25 microns and dried.

21. The composition of claim 20 wherein said pressure sensitive adhesive is present as 0.5 to 5% by weight of said composition.

22. The composition of claim 20 wherein said medicament is present as 0.25 to 20% by weight of said composition.

23. The composition of claim 21 wherein said pressure sensitive adhesive comprises an acrylate.

24. A liquid composition for topical application to the non-mucosal, non-oral, skin and/or hair of a mammal consisting essentially of a solution, emulsion or dispersion of 0.25 to 10% by weight of an oil compatible pressure-sensitive adhesive, 0.1 to 50% by weight of a medicament, and 49.75 to 99.65% by weight of a carrier liquid, the ratio of said polymer to medicament being in the range of 1/5 to 1/50, said composition being non-tacky to the touch and incapable of forming a self-sustaining film when applied as a wet coating of 25 microns and dried.

25. A liquid composition for topical application to the non-mucosal, non-oral, skin and/or hair of a mammal comprising a solution, emulsion or dispersion of 0.25 to 10% by weight of an oil compatible acrylate polymer, 0.1 to 50% by weight of a medicament, and 49.75 to 99.65% by weight of a carrier liquid, the ratio of said polymer to medicament being in the range of 1/5 to 1/50, said composition being non-tacky to the touch when dried and being incapable of forming a self-sustaining film when applied as a wet coating of 25 microns and dried.

* * * * *

UNITED STATES PATENT AND TRADEMARK OFFICE
CERTIFICATE OF CORRECTION

PATENT NO. : 4,940,579

DATED : July 10, 1990

INVENTOR(S) : Randen

It is certified that error appears in the above-identified patent and that said Letters Patent is hereby corrected as shown below:

Column 1, line 10, "continuous of porous" should be --continuous or porous--.

Column 4, line 57, "-CH$_2$COH" should be -- -CH$_2$CO$_2$H --.

Claim 20, column 10, line 8, "0. to 50%" should be -- 0.1 to 50% --.

Signed and Sealed this

Twenty-fourth Day of September, 1991

Attest:

HARRY F. MANBECK, JR.

*Attesting Officer*         *Commissioner of Patents and Trademarks*